(12) United States Patent
Joseph et al.

(10) Patent No.: US 10,709,424 B2
(45) Date of Patent: Jul. 14, 2020

(54) METHOD AND SYSTEM FOR CUFF-LESS BLOOD PRESSURE (BP) MEASUREMENT OF A SUBJECT

(71) Applicant: Healthcare Technology Innovation Centre, Chennai (IN)

(72) Inventors: Jayaraj Joseph, Chennai (IN); Mohanasankar Sivaprakasam, Chennai (IN); Nabeel Pilaparambil Mashood, Chennai (IN)

(73) Assignee: HEALTHCARE TECHNOLOGY INNOVATION CENTRE, Chennai (IN)

( * ) Notice: Subject to any disclaimer, the term of this patent is extended or adjusted under 35 U.S.C. 154(b) by 0 days.

(21) Appl. No.: 15/320,439

(22) PCT Filed: Jun. 18, 2015

(86) PCT No.: PCT/IN2015/000252
§ 371 (c)(1),
(2) Date: Dec. 20, 2016

(87) PCT Pub. No.: WO2015/193917
PCT Pub. Date: Dec. 23, 2015

(65) Prior Publication Data
US 2017/0156706 A1    Jun. 8, 2017

(30) Foreign Application Priority Data
Jun. 20, 2014  (IN) .......................... 3003/CHE/2014

(51) Int. Cl.
*A61B 8/08* (2006.01)
*G16H 50/50* (2018.01)
(Continued)

(52) U.S. Cl.
CPC ........ *A61B 8/5223* (2013.01); *A61B 5/02125* (2013.01); *A61B 8/04* (2013.01);
(Continued)

(58) Field of Classification Search
None
See application file for complete search history.

(56) References Cited

U.S. PATENT DOCUMENTS 5,309,916 A * 5/1994 Hatschek ............... A61B 5/021
600/452
6,676,600 B1 * 1/2004 Conero .................... A61B 5/00
600/438
(Continued)

FOREIGN PATENT DOCUMENTS

WO  WO-2014030174 A3 * 7/2015

*Primary Examiner* — Christopher Koharski
*Assistant Examiner* — James Moss

(57) ABSTRACT

Embodiments herein disclose a method and system for cuff-less blood pressure (BP) measurement of a subject. The method includes measuring, by one or more sensors, a local pulse wave velocity (PWV) and/or blood pulse waveforms of an arterial wall of the subject. Further, the method includes measuring, by an ultrasound transducer, a change in arterial dimensions over a cardiac cycle of the arterial wall of the subject. The arterial dimensions include an arterial distension and an end-diastolic diameter. Furthermore, the method includes measuring, by a controller unit, BP of the subject based on the local PWV and the change in arterial dimensions.

11 Claims, 14 Drawing Sheets

(51) Int. Cl.
*A61B 5/021* (2006.01)
*G06F 19/00* (2018.01)
*A61B 8/04* (2006.01)
A61B 5/107 (2006.01)
A61B 5/00 (2006.01)
A61B 5/02 (2006.01)

(52) U.S. Cl.
CPC ............ *G06F 19/00* (2013.01); *G16H 50/50* (2018.01); *A61B 5/02007* (2013.01); *A61B 5/1075* (2013.01); *A61B 5/6843* (2013.01); *A61B 8/0891* (2013.01)

(56) References Cited

U.S. PATENT DOCUMENTS

| | | | |
|---|---|---|---|
| 7,559,894 B2* | 7/2009 | McEowen | A61B 5/6817 600/438 |
| 2005/0154299 A1* | 7/2005 | Hoctor | A61B 8/4236 600/437 |
| 2015/0223772 A1* | 8/2015 | Shi | A61B 8/0825 600/459 |

* cited by examiner

Sensor 102a  
Sensor 102b  
Sensor 102a  
Ultrasound transducer 104  
Sensor 102b Sensors 102a, 102b and Ultrasonic transducer 104

Desktop Hardware &
Virtual Instrument

Probe   Analog   Probe
        hardware

Laptop   Tablet   Portable
                  device

METHOD AND SYSTEM FOR CUFF-LESS BLOOD PRESSURE (BP) MEASUREMENT OF A SUBJECT

FIELD OF INVENTION

The present invention relates to blood pressure measurement techniques, and more particularly to a mechanism for cuff-less blood pressure (BP) measurement of a subject based on real time acquisition of blood pulse waveforms, measurements of local pulse wave velocity (PWV) and change in arterial dimensions. The present application is a National Phase Application for PCT application No. PCT/IN2015/000252 based on, and claims priority to Indian Application Number 3003/CHE/2014 filed on 20 Jun. 2014, the disclosure of which is hereby incorporated by reference.

BACKGROUND OF INVENTION

Blood Pressure (BP) measurement is a physiological indicator that has found wide spread use in both clinical and non-clinical settings. Usage scenario of BP poses unique functional requirements and challenges. Conventional cuff less method uses two major principles such as tonometry and pulse transit time to measure blood pressure.

In clinical practice, an applanation tonometry is often used which requires an operator to suppress arterial pulsations by externally applied pressure to capture an arterial pressure accurately. The measurement is influenced by an external applied pressure and requires skill to perform correctly. While tonometry is commonly practiced in ophthalmology, its use in measuring arterial blood pressure has remained confined mostly to tertiary clinical care settings and research applications, owing to relatively high cost of devices and skill required to perform accurate measurements.

Devices such as SphygmoCor (AtCor Medicals) utilize tonometry on radial, carotid and femoral arteries along with upper arm cuff measurements for evaluation of central aortic pressure and arterial stiffness by pulse contour analysis. A modification of tonometry principle, integrating an automated mechanism to perform applanation is referred to as vascular unloading and is used by a Finapres device. However, the measurement is performed using photoplethymography sensors on a fingertip and model based techniques are used to reconstruct brachial and aortic pressures, and calibration with an upper arm cuff is required for accurate measurements.

Pulse transit time (PTT) based techniques are the most widely researched in the area of cuff-less BP measurement. The method is based on the relation between BP and PTT, measured by evaluating the time taken by the blood pulse to propagate across a section of the arterial tree. While the basic instrumentation required for this is relatively simple, utilizing dual Photo Plethysmo Graph (PPG) waveforms or a single PPG waveform and ECG signal, the estimation of blood pressure is often performed by model based computation that requires calibration. Most of the existing method of blood pressure measurement uses Moens-Korteweg equation describing the relationship between Pulse Wave Velocity (PWV) and pulse pressure. The PTT based techniques are most commonly used and hence the requirement of population and patient specific calibration limits measurement accuracy, reliability and widespread use.

Although PTT based techniques have the advantage of reduced instrumentation complexity, affordable cost and amenability for a wearable device design, the need of patient specific and population specific calibration to evaluate the constants used in estimation of blood pressure limits measurement accuracy and utility in practice. The requirement of an Electrocardiography (ECG) measurement to accurately measure the PTT is limitation in most systems that need to be addressed to enable wide spread use of the PTT based methods. It may also be remembered that the fundamental relation between the PTT and pressure as described by the Moens-Korteweg or the Bramwell-Hill equation is valid under assumptions of elastic artery walls excited by pulsating pressure with no wave reflections. This is not the case when measurements of PTT are performed at two different points along the arterial tree that has an arterial branching in between. Further, both the viscoelastic nature of vessels and effect of wave reflections tend to affect measurements performed on a peripheral vascular tree (such as radial artery or fingertip) which is the case with most reported systems.

The above information is presented as background information only to help the reader to understand the present invention. Applicants have made no determination and make no assertion as to whether any of the above might be applicable as Prior Art with regard to the present application.

OBJECT OF INVENTION

The principal object of the embodiments herein is to provide a method, system and hand-held device for cuff-less blood pressure (BP) measurement of a subject.

Another object of the invention is to provide a mechanism for measuring a local pulse wave velocity (PWV) of an arterial wall of the subject.

Another object of the invention is to provide a mechanism for measuring a change in arterial dimensions over a cardiac cycle of the arterial wall of the subject.

Another object of the invention is to provide a mechanism to measure BP of the subject based on blood pulse waveforms, the local PWV and the change in arterial dimensions.

SUMMARY

Accordingly the invention provides herein method for cuff-less blood pressure (BP) measurement of a subject. The method includes measuring, by the sensor, a local pulse wave velocity (PWV) and blood pulse waveforms of an arterial wall of the subject. Further, the method includes measuring, by an ultrasound transducer, a change in arterial dimensions over a cardiac cycle of the arterial wall of the subject. The arterial dimensions include an arterial distension and an end-diastolic diameter. Furthermore, the method includes measuring, by a controller unit, the BP of the subject based on the local PWV and the change in arterial dimensions.

Accordingly the invention provides herein a system for cuff-less blood pressure (BP) measurement of a subject. The system includes a probe comprising a first sensor and a second sensor spaced at a distance from said first sensor. The probe includes an ultrasound transducer connected to the first sensor and the second sensor. Further, the system includes a controller unit connected to the probe. The first sensor and the second sensor are configured to measure a local pulse wave velocity (PWV) of an arterial wall of the subject. Further, the ultrasound transducer is configured to measure a change in arterial dimensions over a cardiac cycle of the arterial wall of the subject. The arterial dimensions include an arterial distension and an end-diastolic diameter.

Furthermore, the controller unit is configured to measure BP of the subject based on the local PWV and the change in arterial dimensions.

Accordingly the invention provides herein a hand-held device for a cuff-less Blood Pressure (BP) measurement of a subject. The hand-held device includes a probe configured to be held proximal to skin of the subject. The probe includes a first sensor and a second sensor spaced at a distance from the first sensor. Further, the probe includes a controller unit connected to the first sensor and the second sensor. The first sensor and the second sensor are configured to measure a local pulse wave velocity (PWV) of an arterial wall of the subject. Further, the ultrasound transducer is configured to measure a change in arterial dimensions over a cardiac cycle of the arterial wall of the subject. The arterial dimensions include an arterial distension and an end-diastolic diameter. The blood pulse waveforms and/or local PWV and the change in arterial dimensions are used to measure BP of the subject.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This invention is illustrated in the accompanying drawings, throughout which like reference letters indicate corresponding parts in the various figures. The embodiments herein will be better understood from the following description with reference to the drawings, in which.

DETAILED DESCRIPTION OF INVENTION

Figure 1:
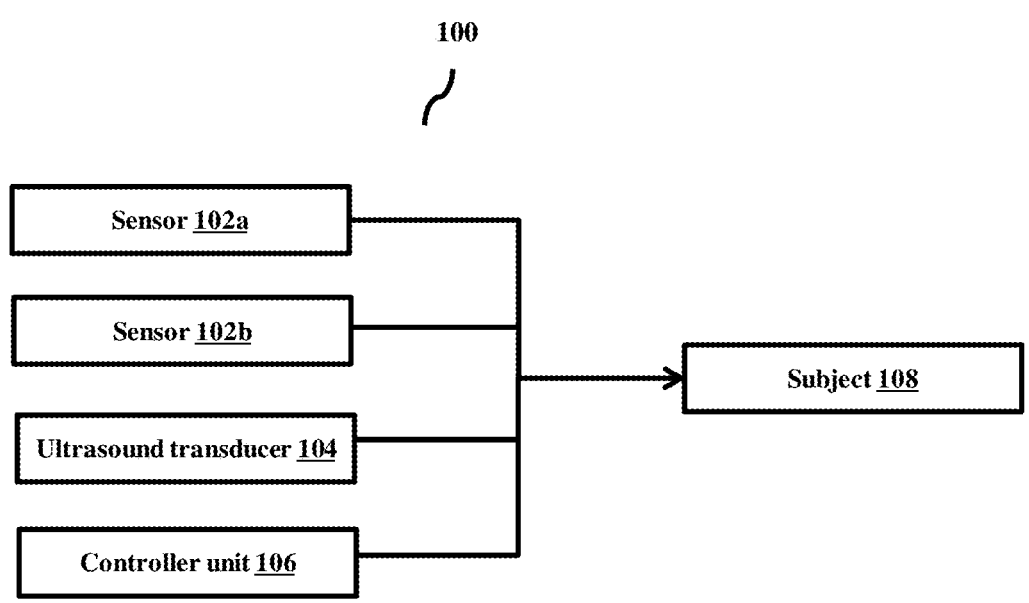
FIG. 1 is a broad overview of a system for cuff less blood pressure (BP) measurement of a subject, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

The embodiments herein achieve a method and system for cuff-less blood pressure (BP) measurement of a subject. The method includes measuring, by a first sensor and a second sensor, a local pulse wave velocity (PWV) of an arterial wall of the subject. Further, the method includes measuring, by an ultrasound transducer, a change in arterial dimensions over a cardiac cycle of the arterial wall of the subject. The arterial dimensions include an arterial distension (ΔD) and an end-diastolic diameter (Dd). Furthermore, the method includes measuring, by a controller unit, BP of the subject based on the local PWV and the change in arterial dimensions.

Unlike convention techniques, the proposed method and system performs a cuff-less calibration free measurement of non-invasive blood pressure of the subject in an easy manner. The proposed method uses various measurement techniques to evaluate blood pressure by utilizing a combination of sensors (ultrasound, pulse sensors, pressure sensors and so on) and different mathematical models to derive the blood pressure of the subject.

Unlike conventional systems, the proposed method and system measures the local PWV, the Dd and the ΔD, along with mathematical models developed based on established physics of arterial wall dynamics. This allows evaluation of systolic and diastolic pressure on a superficial artery (such as the carotid and brachial) of the subject, without the need of any patient specific or population specific calibration coefficients.

The proposed method measures the arterial dimensions along with a Pulse transit time (PTT) that allows direct computation of systolic and diastolic blood pressures without the need of any patient specific or population specific calibration coefficients. The cuff-less BP measurement method can be used on any superficial artery, such as carotid or femoral artery and does not require extensive expertise to perform measurement. The proposed cuff-less BP measurement method can be used for carotid, brachial, femoral arteries and so on. Further, the proposed method provides quick and easy measurement.

The proposed method provides simultaneous measurement of dual pulse waveforms using either the trimodal or bimodal BP probe, so as to eliminate the need of additional ECG connections while performing the measurements.

The method measures the PWV over a small section of the artery, and all relevant variables from a systolic rise region of the measured pulse wave. This eliminates the effect of wave reflections and viscoelasticity of walls. Thus results in ensuring that the fundamental assumptions of B-H equation hold true during measurements and reduces measurement error.

Referring now to the drawings, and more particularly to FIGS. 1 through 9e, where similar reference characters denote corresponding features consistently throughout the figures, there are shown preferred embodiments.

FIG. 1 is a broad overview of a system 100 for cuff less BP measurement of a subject 108, according to embodiments as disclosed herein. In an embodiment, the subject 108 can be a patient. The system 100 includes a set of sensors 102a, 102b (hereinafter referred as 102), an ultrasound transducer 104, and a controller unit 106. The sensor 102 can be for example, but not limited to, an ultrasound sensor, a pulse sensor, a pressure sensor, a piezoelectric sensor, a photo plethysmo graph sensor, a magnetic plethysmo graph sensor, a magnetic sensor, a force sensitive sensor and so on. The sensor 102 detects a first pulse waveform at first site along an artery wall. Further, the sensor 102 detects a second pulse waveform at a second site along the artery wall. In an embodiment, the first site and the second site are spaced at a distance along the artery wall. In an embodiment, the sensor 102 detects the first and second pulse waveforms at a same site along the artery wall. Based on detecting the first and second pulse waveforms at the first site and the second site along the artery wall, the sensor 102 measures a local pulse wave velocity (PWV) of the arterial wall of the subject 108.

The ultrasound transducer 104 placed in between a first sensor and a second sensor in the set of sensors.

In an embodiment, the ultrasound transducer 104 is placed at a center of a third sensor in the probe. In an embodiment, the third sensor is a ring force sensor and configured to provide feedback to the controller unit 106 to measure BP of the subject.

In another embodiment, the ultrasound transducer 104 is coupled to the first sensor using a coupling mechanism. In an embodiment, the first sensor is a flexible force sensor.

Further, the ultrasound transducer 104 sends ultrasound signals through body of the subject 108. After sending ultrasound signals through body of the subject 108, the ultrasound transducer 104 obtains the reflected ultrasound signals from a near arterial wall and a far arterial wall. Based on obtaining the reflected ultrasound signals from the near arterial wall and the far arterial wall, the ultrasound transducer 104 converts the ultrasound signals to corresponding voltage pulses. After converting the ultrasound signals to corresponding voltage pulses, the ultrasound transducer 104 splits the voltage pulses into a set of frames. In an embodiment, the ultrasound transducer 104 detects a location of the arterial wall based on the motion profile signal identified from the set of frames.

In an embodiment, based on detecting the location of the arterial wall, the ultrasound transducer 104 tracks the motion of the arterial wall from a frame to a subsequent frame. In an embodiment, the frame and the subsequent frame are selected from the set of frames. After tracking the motion of the arterial wall from the frame to the subsequent frame, the ultrasound transducer 104 measures an arterial distension ($\Delta D$) based on a difference between the near arterial wall and the far arterial wall.

In an embodiment, the ultrasound transducer 104 measures an end-diastolic diameter ($D_d$) across a vessel towards end of a diastole.

The ultrasound transducer 104 measures a change in arterial dimensions over a cardiac cycle of the arterial wall of the subject 108. In an embodiment, the arterial dimensions include the arterial distension ($\Delta D$) and the end-diastolic diameter ($D_d$). A controller unit 106 measures BP of the subject 108 based on the local PWV and the change in the arterial dimensions.

The FIG. 1 illustrates a limited overview of the system 100, but it is to be understood that other embodiments are not limited thereto. The labels or names of the units are used only for the illustrative purpose and does not limit the scope of the invention. Further, in real-time the function of the one or more units can be combined or separately executed by the same or other units without departing from the scope of the embodiments described herein. Further, the system 100 can include various other units along with other hardware or software components communicating locally or remotely to control the dynamic operation of the system 100. For example, the component can be, but not limited to, a process running in the controller or processor, an object, an executable process, a thread of execution, a program, or a computer.

Figure 2A:
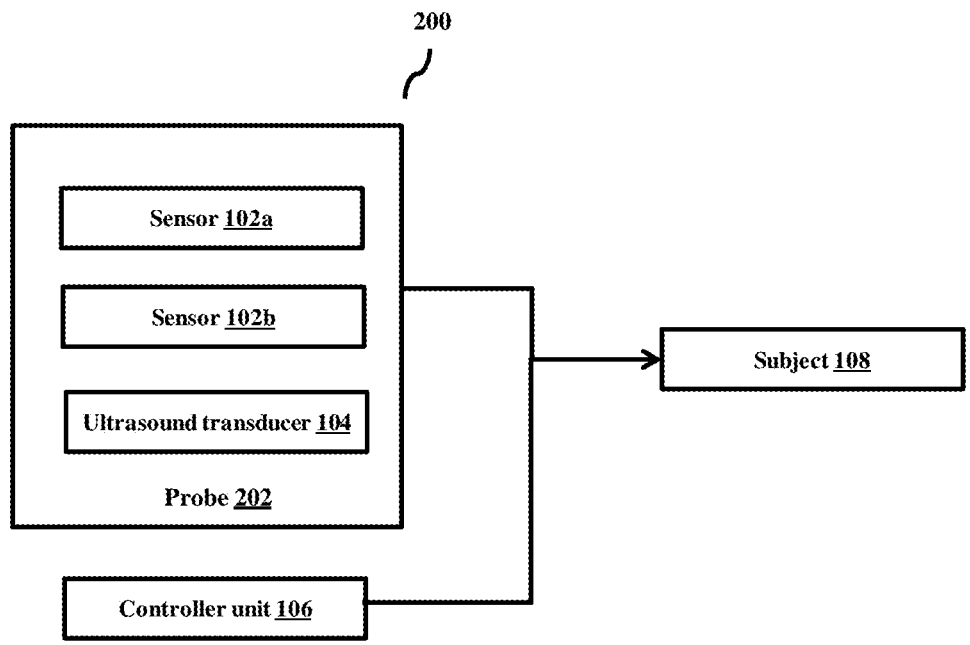
FIG. 2a is an overview of a hand-held device for cuff less BP measurement of the subject, according to embodiments as disclosed herein.

FIG. 2a is an overview of a hand-held device 200 for cuff less BP measurement of the subject 108, according to embodiments as disclosed herein. The operation and function of the sensors 102a and 102b, the ultrasound transducer 104, and the controller unit 106 remain same as described in the FIG. 1. In the FIG. 2a, the hand-held device 200 includes a probe 202 configured to be held proximal to skin of the subject 108. In an embodiment, the probe 202 includes the sensors 102a and 102b, and the ultrasound transducer 104. The probe 202 is arranged external to the controller unit 106.

Figure 2B:
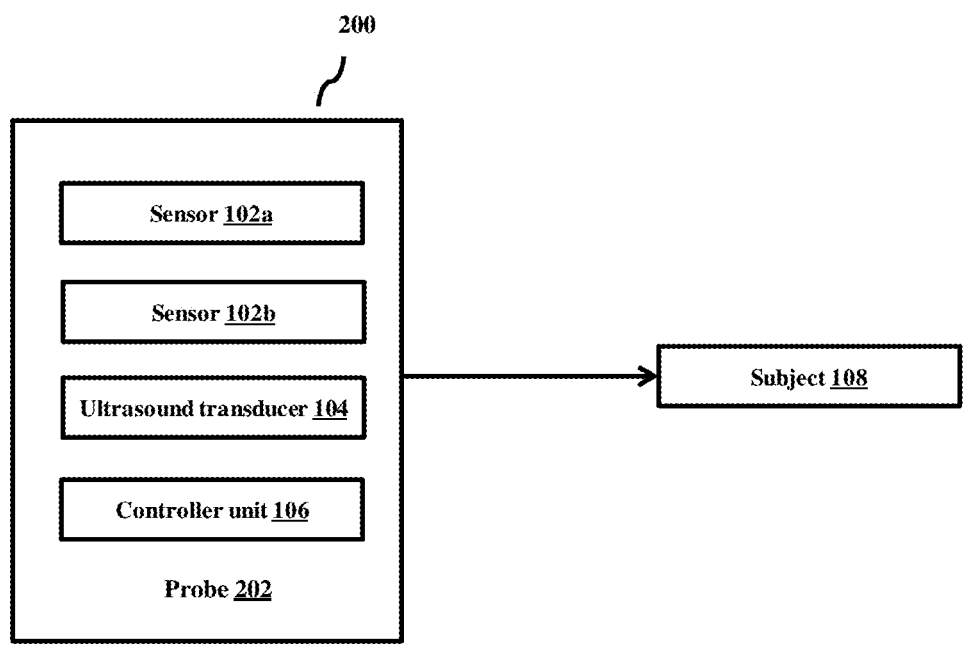
FIG. 2b is an overview of a hand-held device for cuff less BP measurement of the subject, according to embodiments as disclosed herein.

In the FIG. 2b, the hand-held device 200 includes the probe 202 is configured to be held proximal to skin of the subject 108. In an embodiment, the probe 202 includes the sensors 102a and 102b, the ultrasound transducer 104, and the controller unit 106. The operation and function of the sensors 102a and 102b, the ultrasound transducer 104, and the controller unit 106 remains same as described in the FIG. 1.

The FIGS. 2a and 2b illustrates the limited overview of the hand-held device 200, but it is to be understood that other embodiments are not limited thereto. The labels or names of the units are used only for the illustrative purpose and does not limit the scope of the invention. Further, in real-time the function of the one or more units can be combined or separately executed by the same or other units without departing from the scope of the embodiments described herein. Further, the hand-held device 200 can include various other units along with other hardware or software components communicating locally or remotely to control the dynamic operation of the hand-held device 200. For example, the component can be, but not limited to, a process running in the controller or processor, an object, an executable process, a thread of execution, a program, or a computer.

Figure 3:
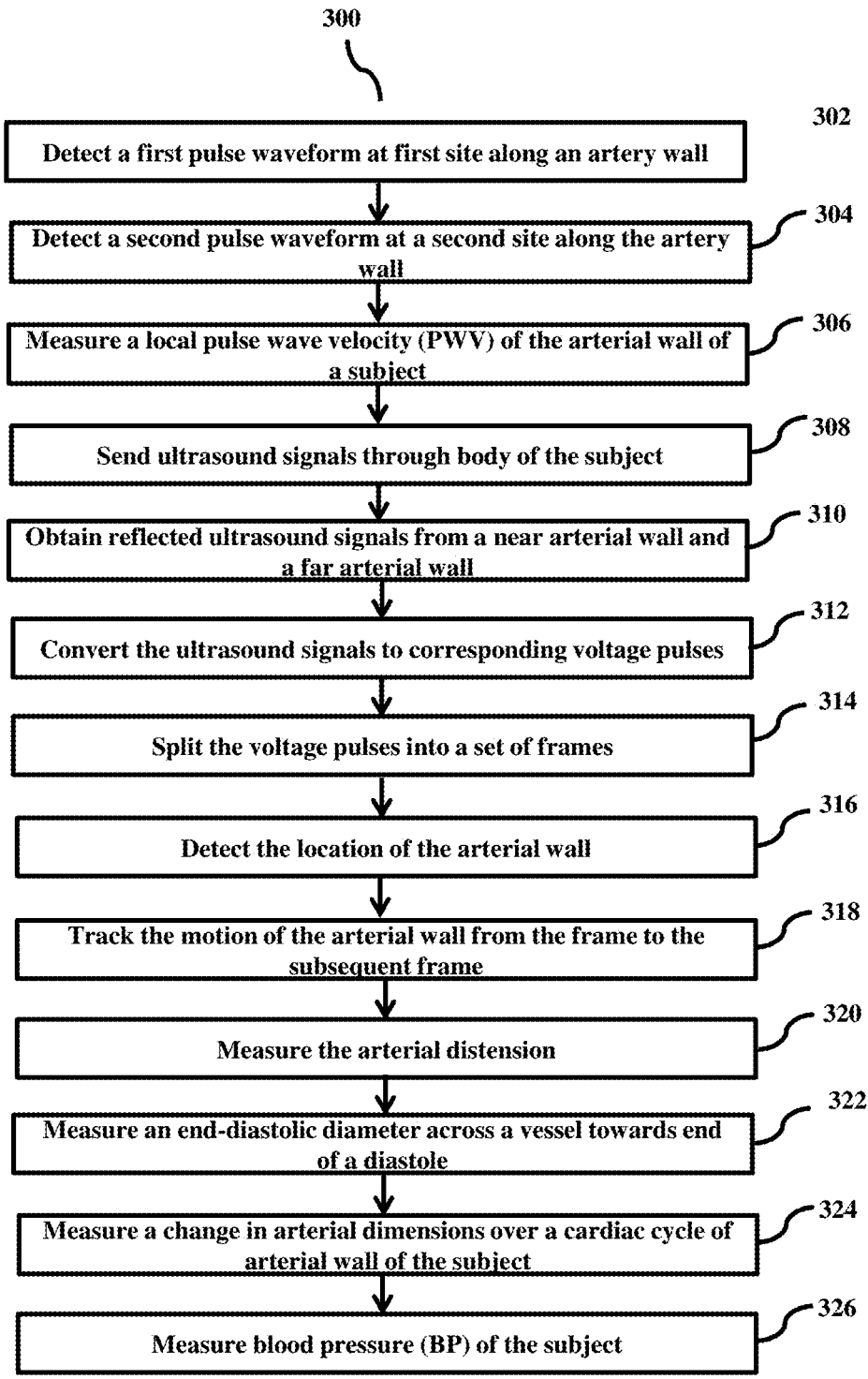
FIG. 3 is a flow diagram explaining a method for cuff less BP measurement of the subject, according to embodiments as disclosed herein.

FIG. 3 is a flow diagram explaining a method 300 for cuff-less BP measurement of the subject 108, according to embodiments as disclosed herein. At step 302, the method 300 includes detecting a first pulse waveform at the first site along the artery wall. In an embodiment, the method 300 allows the sensor 102 to detect the first pulse waveform at the first site along the artery wall. The sensor 102 can be for example, but not limited to, an ultrasound sensor, a pulse sensor, a pressure sensor, a piezoelectric sensor, a Photoplethysmograph sensor, a magnetic plethysmograph sensor, a magnetic sensor and so on.

At step 304, the method 300 includes detecting the second pulse waveform at the second site along the artery wall. In an embodiment, the method 300 allows the sensor 102 to detect the second pulse waveform at the second site along the artery wall. In an embodiment, the first site and the second site are spaced at the distance along the artery wall. In an embodiment, the sensor 102 is configured to detect the first and second pulse waveform at the same site along the artery wall.

At step 306, the method 300 includes measuring the local pulse wave velocity (PWV) of the arterial wall of the subject 108. In an embodiment, the method 300 allows the sensor 102 to measure the local pulse wave velocity (PWV) of the arterial wall of the subject 108 by computing a time difference between the first pulse waveform and the second pulse waveform.

At step 308, the method 300 includes sending ultrasound signals through body of the subject 108. In an embodiment, the method 300 allows the ultrasound transducer 104 to send ultrasound signals through body of the subject 108. At step 310, the method 300 includes obtaining reflected ultrasound signals from the near arterial wall and the far arterial wall. In an embodiment, the method 300 allows the ultrasound transducer 104 to obtain reflected ultrasound signals from the near arterial wall and the far arterial wall.

At step 312, the method 300 includes converting the ultrasound signals to corresponding voltage pulses. In an embodiment, the method 300 allows the ultrasound transducer 104 to convert the ultrasound signals to corresponding voltage pulses. At step 314, the method 300 includes splitting the voltage pulses into the set of frames. In an embodiment, the method 300 allows the ultrasound transducer 104 to split the voltage pulses into the set of frames.

At step 316, the method 300 includes detecting the location of the arterial wall based on the motion profile signal identified from the frames. In an embodiment, the method 300 allows the ultrasound transducer 104 to detect the location of the arterial wall based on the motion profile signal identified from the frames.

At step 318, the method 300 includes tracking the motion of the arterial wall from the frame to the subsequent frame. In an embodiment, the method 300 allows the ultrasound transducer 104 to track the motion of the arterial wall from the frame to the subsequent frame. The frame and said subsequent frame are selected from the set of frames.

At step 320, the method 300 includes measuring the arterial distension. In an embodiment, the method 300 allows the ultrasound transducer 104 to measure the arterial distension based on the difference between the near arterial wall and the far arterial wall.

At step 322, the method 300 includes measuring the end-diastolic diameter across the vessel towards end of the diastole. In an embodiment, the method 300 allows the ultrasound transducer 104 to measure the end-diastolic diameter across the vessel towards end of the diastole.

At step 324, the method 300 includes measuring the change in the arterial dimensions over the cardiac cycle of the arterial wall of the subject 108. In an embodiment, the method 300 allows the ultrasound transducer 104 to measure the change in the arterial dimensions over the cardiac cycle of the arterial wall of the subject 108.

At step 326, the method 300 includes measuring BP of the subject 108 based on the local PWV and the change in the arterial dimensions. In an embodiment, the method 300 allows the controller unit 106 to measure BP of the subject 108 based on the local PWV and the change in arterial dimensions.

The various actions, acts, blocks, steps, and the like in the method 300 may be performed in the order presented, in a different order or simultaneously. Further, in some embodiments, some actions, acts, blocks, steps, and the like may be omitted, added, modified, skipped, and the like without departing from the scope of the invention.

Figure 4:
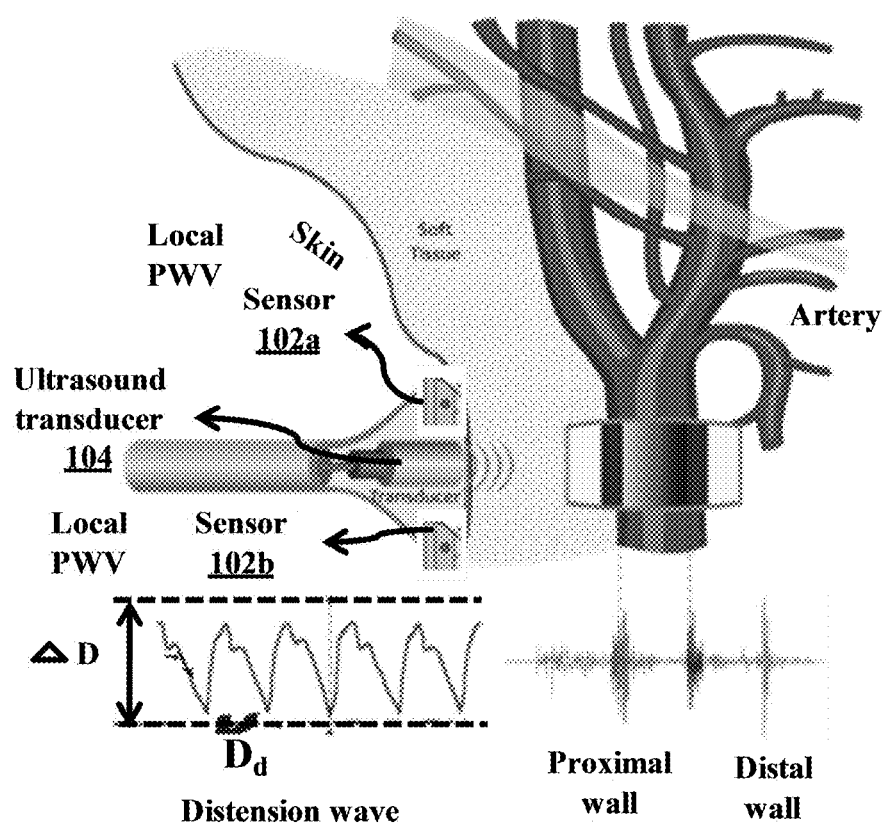
FIG. 4 shows a schematic representation of an image free ultrasound based BP measurement, according to embodiments as disclosed herein.

FIG. 4 shows a schematic representation of an image free ultrasound based BP measurement, according to embodiments as disclosed herein. The image free ultrasound BP measurement is based on the measurement of the local PWV across a small section of the superficial artery, and changes in arterial dimensions at the measurement site. FIG. 4 shows the sensor 102a, the sensor 102b and the ultrasound transducer 104 which are placed in the skin of the subject 108. The local PWV is measured by detecting two pulse waveforms at two sites along the artery wall, by utilizing the sensor 102a and the sensor 102b.

By measuring the time delay ($\Delta t$) between the two pulse waveforms measured at two sites, spaced at a distance l, the local PWV may be measured as in equation (1).

$$\text{Local PWV}=1/\Delta t \tag{1}$$

The changes in arterial dimensions at the measurement site are detected using the ultrasound transducer 104 operating in the pulse echo modality. The ultrasound transducer 104 can be a high frequency ultrasound transducer. The ultrasound transducer 104 is configured to send high frequency pulses of sound into the artery wall. The echoes reflected from the arterial walls are detected by the ultrasound transducer 104, and are processed using an technique to detect and track wall motion and capture the arterial distension waveform disclosed in application number 3485/CHE/2012 titled "Automated evaluation of arterial stiffness for a non-invasive screening". The end-diastolic diameter (Dd), the arterial distension over the cardiac cycle ($\Delta D$) as well as the arterial distension waveform D(t) that describes the instantaneous changes in the arterial diameter over each cardiac cycle are captured in this measurement.

In an embodiment, the ultrasound transducer 104 and the sensors 102a and 102b are placed in different position to measure the local PWV, the end-diastolic diameter and the arterial distension over the cardiac cycle ($\Delta D$).

Figure 5:
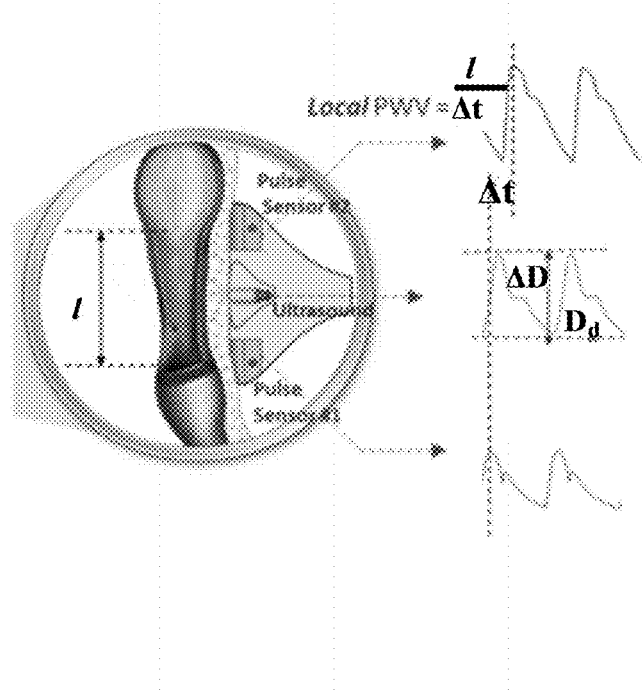
FIG. 5 shows the components to measure local Pulse Wave Velocity (PWV), an end-diastolic diameter (Dd), and an arterial distension over a cardiac cycle (ΔD) to directly measure the BP of the subject, according to embodiments as disclosed herein.

FIG. 5 shows the components to measure local PWV, the end-diastolic diameter (Dd), and the arterial distension over the cardiac cycle ($\Delta D$) to directly measure the blood pressure of the subject 108, according to embodiments as disclosed herein. In an embodiment, the pulse wave sensors (sensors 102a and 102b) and ultrasound transducer 104 are placed in same position to measure the local PWV, the Dd, and the $\Delta D$. Since the artery is elastic, the pulsations of the artery are related to the transmural blood pressure and its material properties. The well established Bramwell-Hill (equation 2) relates this PWV to blood pressure. However, this is true only for a small section of the artery.

$$PWV, c = \frac{l}{PTT} = \sqrt{\frac{V}{\rho \frac{dV}{dP}}} \quad (2)$$

The proposed method measures the local PWV, the Dd, and the ΔD required for evaluation of blood pressure of the subject 108 obtained from two pulse waveforms and the arterial distension waveform measured at the same site. In an embodiment, the measurements are obtained through a simultaneous measurement or a sequential measurement described below.

Simultaneous Measurement:

The two pulse waveforms required for computation of the local PWV, and the arterial distension waveform are measured simultaneously. The Local PWV and the arterial distension waveform are measured using a tri-modal blood pressure probe that integrates dual pulse sensors along with the ultrasound transducer 104 into a single probe. This is the preferred modality of measurement, as it ensures that arterial dimension measurements are performed simultaneously with the pulse propagation measurements. Further, there is no ambiguity in path length measurements in this method as it is a constant determined by the dimensions of the probe.

Sequential Measurement:

The dual pulse waveforms and the arterial distension waveform are measured in a sequential manner. This may be performed in any of the following methods.

Pulse Sensor, Ultrasound Transducer and ECG Electrodes:

This method requires the connection of ECG electrodes to the subject 108. The single pulse sensor may be utilized to detect the upstream and downstream pulse waveforms in two consecutive measurements. A Pulse Arrival Time (PAT) of the blood pulse wave at each of these measurement sites are measured as the time delay from a R-peak of the ECG signal to the foot of the pulse waveform. Difference between the two PAT values gives the local PTT which is used to compute the local PWV. The arterial distension waveform may be measured using the ultrasound transducer 104 subsequent to the local PWV measurements.

Ultrasound Transducer with ECG:

This method also requires connection of ECG electrodes to the subject 108. A single element ultrasound transducer probe may be used to capture the arterial distension waveforms at two points along the arterial tree. Using ECG signal as the reference, the local PWV may be computed, which along with arterial dimensions will allow evaluation of the blood pressure.

Using ultrasound compliance probe with integrated ECG:

This method requires the utilization of a bi-modal compliance probe that has the ECG electrode integrated along with the ultrasound transducer 104 used for arterial dimension measurements. Sequential measurement of the arterial distension waveform at two sites along the arterial tree, with simultaneous recording of the ECG signal utilizing the integrated ECG electrode can provide the local PWV and arterial dimensions required for evaluation of blood pressure.

Figure 6A:
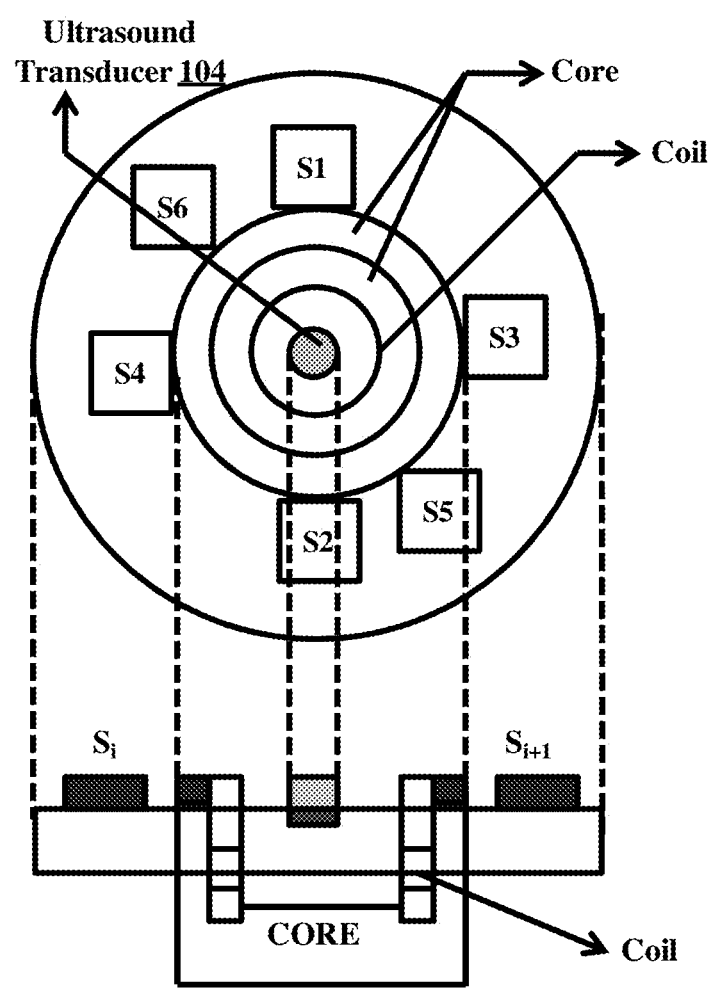
FIG. 6a illustrates an example design of an arterial compliance probe utilizing an array of magnetic sensors, according to embodiments as disclosed herein.

FIG. 6*a* illustrates an example design of an arterial compliance probe utilizing an array of magnetic sensors, according to embodiments as disclosed herein. The magnetic sensors (S1, S2, S3 and S4) are placed equidistant from an electronically controlled magnetic field source (coil), with the ultrasound transducer 104 positioned at the center of the array, equidistant from all the magnetic sensing elements. In an embodiment, the probe utilizes dual Magnetic Plethysmo graph (MPG) sensors to capture the two pulse waveforms. The MPG sensors typically consists of a small magnet (electromagnet/permanent) that establishes an ambient field and a magnetic field sensor (such as a Hall sensor or a Giant Magneto Resistance sensor or Tunnel magneto resistance (TMR)) to detect the pulse waveform.

In an embodiment, the shape of the core is cylindrical. The coil is wound over the magnetic field excitation coil.

The array configuration shown in FIG. 6*a* obtains the blood flow pulse waveform easily due to the larger number of sensors. At any given instant, when the probe is placed over a section of the artery, and pairs of sensors located diametrically opposite positions ($S_i$, $S_{i+1}$) provides a strong bio-signal output. The ultrasound transducer 104 located at the center of the array would be positioned over the artery segment covered by the compliance probe. With the proposed configuration, the magnetic sensor array ensures that the ultrasound transducer 104 is positioned correctly over the artery section for measurement of the arterial distension.

Figure 6B:
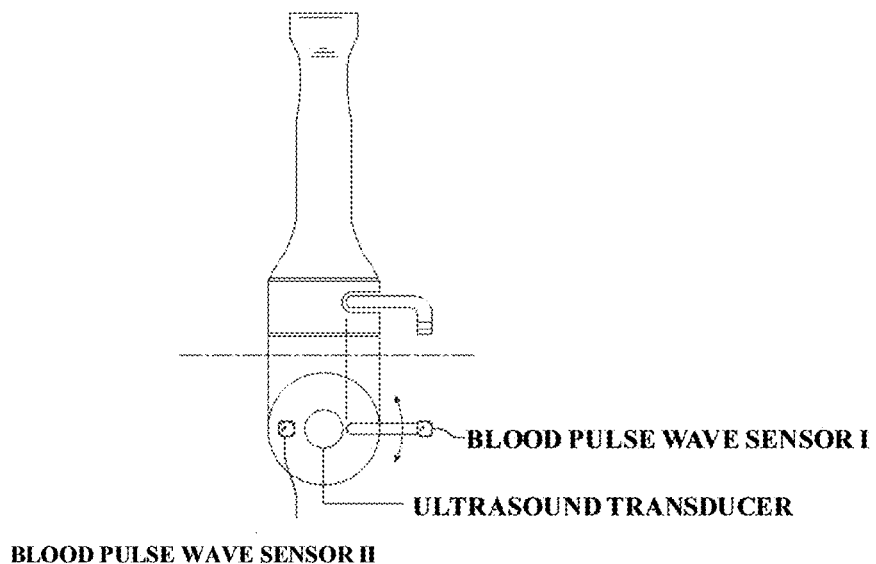
FIG. 6b illustrates another example design of an arterial compliance probe, according to embodiments as disclosed herein.

FIG. 6*b* illustrates an example design of an arterial compliance probe, according to embodiments as disclosed herein. The arterial compliance probe shown in FIG. 6*b* includes a blood pulse wave sensor 1, blood pulse wave sensor 2 and an ultrasound sensor. In an embodiment, the blood pulse wave sensors 1 and 2 can be the pressure sensors, the MPG sensors and the like. The blood pulse wave sensor 1 and blood pulse wave sensor 2 are used to measure the local PWV and the ultrasound transducer 104 measures the arterial distensions (Dd and ΔD). Using the measured values of the local PWV, and the arterial distensions, the proposed method uses the mathematical models to compute the blood pressure of the subject 108.

Figure 6C:
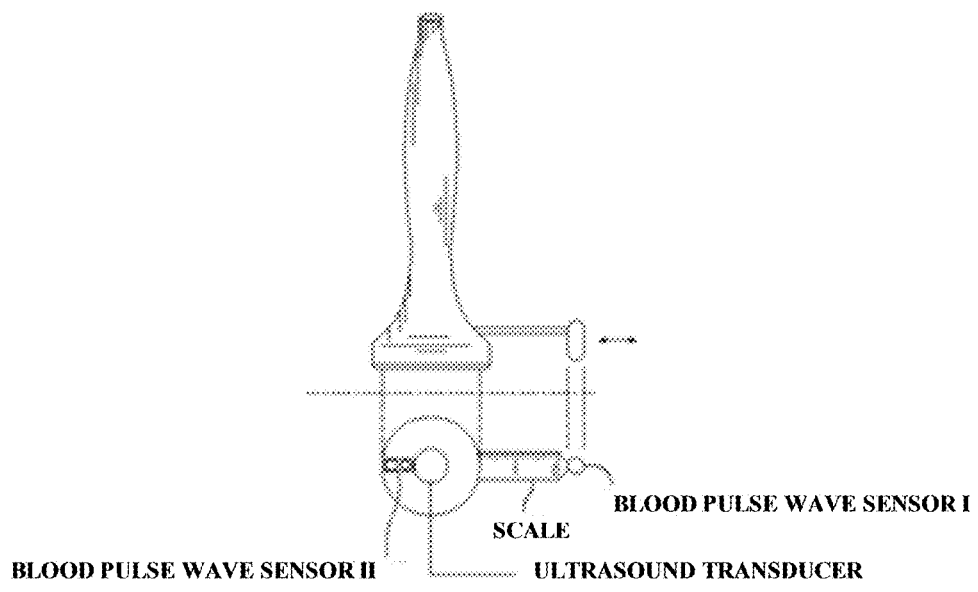
FIG. 6c illustrates another example design of an arterial compliance probe with a scale, according to embodiments as disclosed herein.

FIG. 6*c* illustrates an example design of an arterial compliance probe with a scale, according to embodiments as disclosed herein. The arterial compliance probe shown in the FIG. 6*c* includes the blood pulse wave sensor 1, the blood pulse wave sensor 2 and the ultrasound sensor. Further, the design shown in the FIG. 6*c* includes a scale. In an embodiment, the blood pulse wave sensors can be the pressure sensors, the MPG sensors and the like. The blood pulse wave sensor 1 and the blood pulse wave sensor 2 are used to measure the local PWV and the ultrasound transducer 104 measures the arterial distensions (Dd and ΔD). Using the measured values of the local PWV, and the arterial distensions, the proposed method uses the mathematical models to compute the blood pressure of the subject.

Figure 6D:
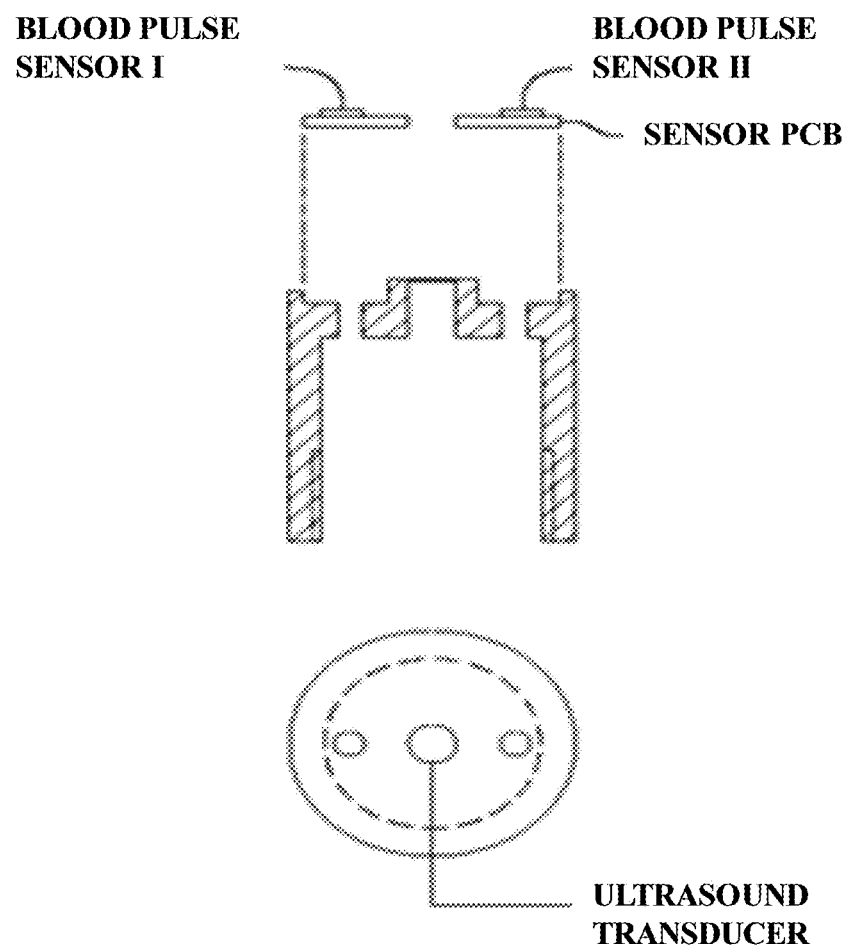
FIGS. 6d-6f illustrate another example designs of an arterial compliance probe, according to embodiments as disclosed herein.

FIG. 6*d* illustrates an example design of the arterial compliance probe with sensor PCB attached to a sensor holder of the probe and ultrasound transducer 104. In an embodiment, the blood pulse sensor can be any blood pulse transducers such as MPG, PPG, and flexible circular force sensor and so on.

Figure 6E:
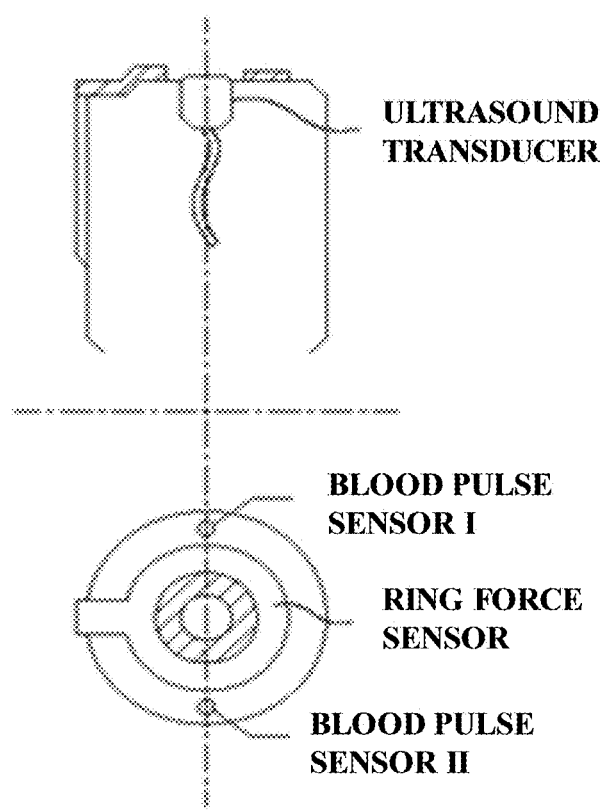

FIG. 6*e* illustrates another example design of the arterial compliance probe. As shown, the probe design includes a flexible ring force sensor and the ultrasound transducer is placed at the center of the ring force sensor. In an example, the flexible ring force sensor is a ring shaped FSR. In an embodiment, the signal from the ring force sensor can be used to provide feedback to the operator after applying intelligent algorithms on the pressure waveforms so that operator can apply the right amount of pressure on the probe.

In another embodiment, the signal from the ring force sensor can be used to provide feedback that can be used in developed BP measurement mathematical models as surface pressure waveform.

Figure 6F:
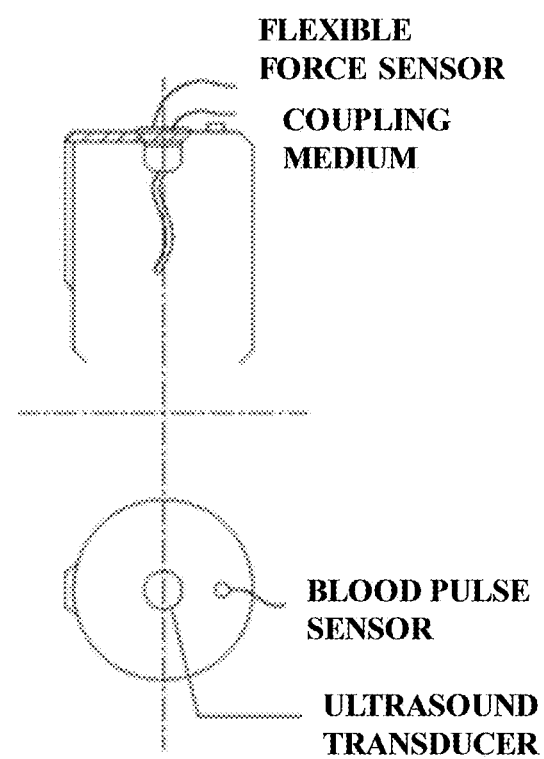

FIG. 6f illustrates another example design of an arterial compliance probe, according to embodiments as disclosed herein. As shown, a flexible circular force sensor (FSR) is placed at the top of ultrasound transducer 104 with a suitable coupling medium. The probe design allows acquisition of surface pressure waveform and distention waveform from the same location simultaneously. In an embodiment, the FSR output and blood pulse signal output (from sensors 102) can be used for local PWV measurement also.

Figure 7:
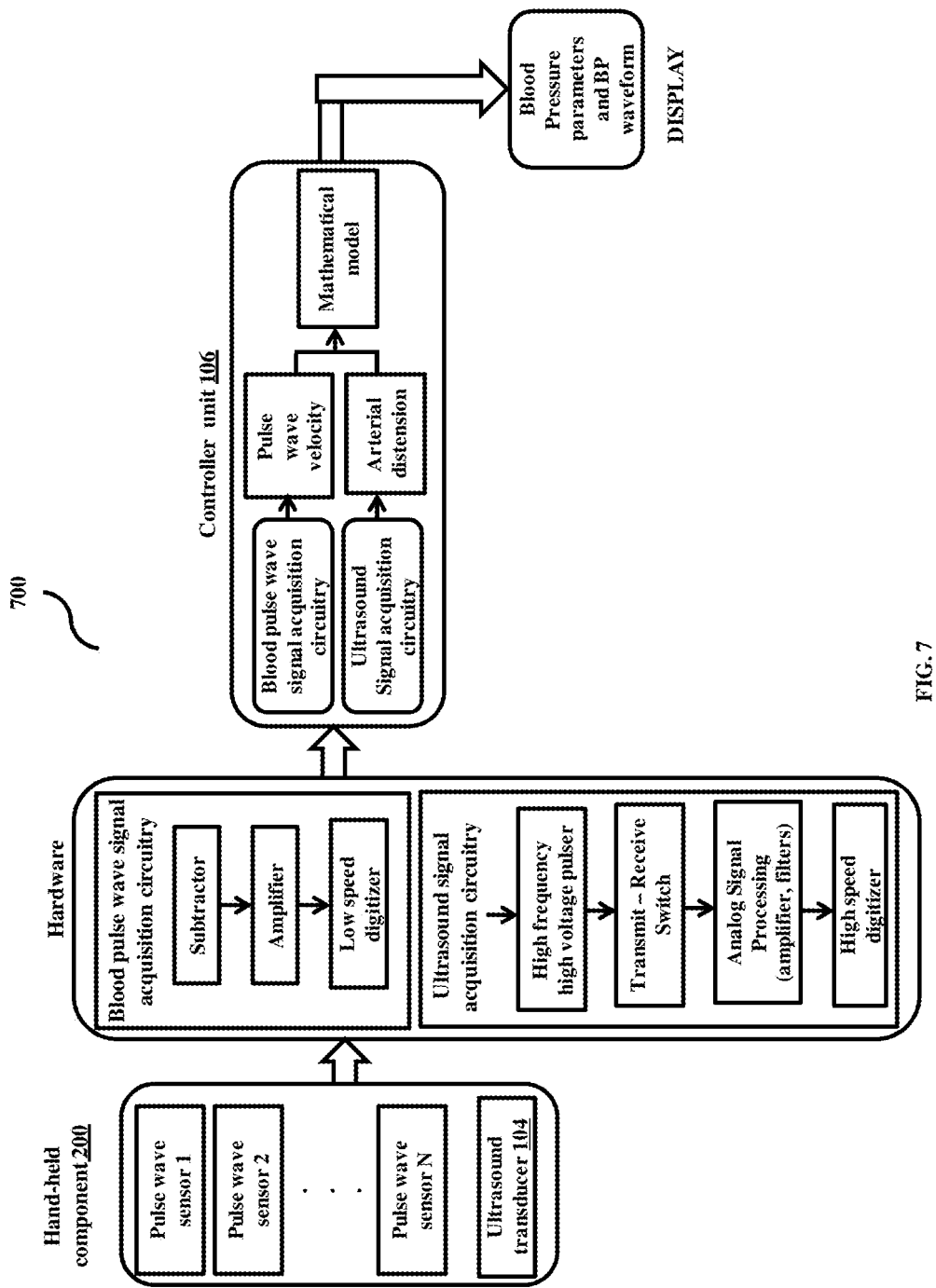
FIG. 7 shows an overview of a system for measuring the BP of the subject, according to embodiments as disclosed herein.

FIG. 7 shows an overview of a system 700 for measuring the blood pressure of the subject 108, according to embodiments as disclosed herein. The system 700 includes the hand-held component 200, a hardware unit, the controller unit 106 and a display. In an embodiment, the hand-held component 200 includes a plurality of pulse wave sensors (1, 2, 3 . . . N) and the ultrasound transducer 104. The pulse wave sensors measure the local PWV and the ultrasound transducer 104 measures the changes in the arterial dimensions (end-diastolic diameter (Dd), the arterial distension over the cardiac cycle ($\Delta D$)). The measured values are input into the hardware unit which includes a blood pulse wave signal acquisition circuitry and a signal acquisition circuitry.

In an embodiment, the blood pulse wave signal acquisition circuitry includes modules such as a subtractor, an amplifier and a low speed digitizer. A person of ordinary skill in the art should appreciate that the blood pulse wave signal acquisition circuitry is not limited to the modules mentioned above and may have various other modules.

In an embodiment, the ultrasound signal acquisition circuitry includes modules such as a high frequency high voltage pulser, a Transmit-Receive Switch, a Analog Signal Processing (amplifier, filters), and a High speed digitizer. A person of ordinary skill in the art should appreciate that the blood pulse wave signal acquisition circuitry is not limited to the modules disclosed above and may have various other modules.

The output of the blood pulse wave signal acquisition circuitry and the ultrasound signal acquisition circuitry are input into the controller unit 106. The controller unit 106 computes the local PWV and the arterial distension and performs mathematical modeling to evaluate the blood pressure of the subject 108. The methods of mathematical modeling are given below. The proposed method utilizes any one of the method to compute the blood pressure. Further, the blood Pressure parameters and BP waveform is displayed on the display.

Method-1: Based on Continuous Measurement of PWV and Hughes' Relationship.

The pulse pressure is computed using below equation 3 derived from the Bramwell-Hill equation for local pulse wave velocity.

$$\text{Pulse pressure}, \Delta P = P_s - P_d = (PWV)^2 2\rho(\Delta D/D_d) \quad (3)$$

Direct measurement of arterial distension ($\Delta D$), end diastolic diameter (Dd), and local PWV, along a section of the artery (to minimize effects of wave reflection and ensure validity of elastic artery walls assumed in B-H equation) allows calibration free measurement of pulse pressure using equation 4.

Method-1 uses Moens-Korteweg equation for measuring local PWV, Hughes relation between Young's modulus and blood pressure and also the Meinders-Hoeks exponential relationship between blood pressure and artery cross section. The above mentioned relationships are utilized to eliminate the patient specific parameters to arrive at an equation for systolic pressure as below.

$$P_S \ln\left(\frac{P_S}{P_S - \Delta P}\right) = \frac{\left(\frac{(D_S^2 - D_D^2)}{\alpha D_S C_S^2}\right)\left(\frac{d}{dt}(D_{(t)} C_{(t)}^2)\big|_{t=t_S}\right)}{\frac{d}{dt}(D_{(t)}^2)\big|_{t=t_s}} \quad (4)$$

where, $C_S$ is the local pulse wave velocity evaluated at the systole and $C(t)$ is the local pulse wave velocity waveform measured at every point within the cardiac cycle.

Right hand side of the equation 4 is evaluated from measurements. Utilizing the $\Delta P$ value computed from equation 3, the value of $P_S$ is obtained, which is the systolic pressure. Now, diastolic pressure $P_D = P_S - \Delta P$.

Method-2: Based on Incremental Pressure Measurements, Continuous PWV and Meinders-Hoeks Relationship.

In method-2, the incremental pressure difference $\delta P(t)$ at any given time instant within the cardiac cycle, from the end-diastolic pressure is evaluated using equation 5 mentioned below.

$$\delta P_{(t)} = \frac{2\rho}{D_D} C_{(t)}^2 \Delta D_{(t)} \quad (5)$$

where,
$D_D$: Diastolic diameter
$D_S$: Systolic diameter
$C_S$: Pulse wave velocity at systolic point
$C_x$: Pulse wave velocity at some point 'x', other than diastolic point
$D_x$: Diameter that corresponds to $C_x$.

Using equation 5and above measured parameters, the pulse pressure $\Delta P$ and $\delta Px$ are calculated. Then the diastolic pressure, $P_D$ is calculated by solving the following equation 6 mentioned below.

$$\frac{\ln\left(1 + \frac{\delta P_x}{P_D}\right)}{\ln\left(1 + \frac{\Delta P}{P_D}\right)} = \frac{D_x^2 - D_D^2}{D_S^2 - D_D^2} = \lambda \text{ (a constant for } D_x\text{)} \quad (6)$$

Now, systolic pressure is, $P_S = P_D + \Delta P$

Method-3: Based on Incremental Pressure Measurements and Single Point PWV.

In method-3, the local PWV is measured at one critical point within the cardiac cycle and assumed to be a constant C. Typically the PWV measurement is performed at the point where the first derivative of the pulse waveform is maximum. Now, the incremental pressure, $\delta P(t)$ at any instant within the cardiac cycle is calculated as in the equation 7 mentioned below.

$$\delta P_{(t)} = 2\rho C^2 \ln\left(\frac{D_{(t)}}{D_D}\right) \quad (7)$$

where,
$D_D$: Diastolic diameter.
$D_S$: Systolic diameter.
C: Pulse wave velocity $D_x$ Diameter measured at some point in between systolic and diastolic.

Using equation 7 and above measured parameters, calculate $\Delta P$ and $\delta P_x$. Then, solve equation 8 to find diastolic pressure $P_D$.

$$\frac{\ln\left(1+\frac{\delta P_x}{P_D}\right)}{\ln\left(1+\frac{\Delta P}{P_D}\right)} = \frac{D_x^2 - D_D^2}{D_S^2 - D_D^2} = \lambda \text{ (a constant for } D_x\text{)} \quad (8)$$

Method-4: Based on Tonometry and Single Point Local PWV Measurement

In this method, the output waveforms obtained from two pulse transducers, are used for calculation of PWV at one point within the cardiac cycle as in Method-3. The pulse pressure is then calculated using the equation 9 mentioned below.

$$\Delta P = P_S - P_D = C^2 2\rho(\Delta D/D_D) \quad (9)$$

The pressure sensor is used as one of the pulse sensors to detect a pressure waveform, f(t) which is used to model the blood pressure waveform as P(t)=a+b f(t), where 'a' and 'b' are two constants. Now, utilizing the Meinders-Hoeks relationship, derive the equation 10 mentioned below.

$$\frac{\ln\left(\frac{1+\left(\frac{b}{a}\right)f_x}{1+\left(\frac{b}{a}\right)f_D}\right)}{\ln\left(\frac{1+\left(\frac{b}{a}\right)f_S}{1+\left(\frac{b}{a}\right)f_D}\right)} = \frac{D_x^2 - D_D^2}{D_S^2 - D_D^2} \quad (10)$$

where, $D_S$: Systolic diameter
$D_D$: Diastolic diameter
$D_x$: Diameter at any point, x, within the cardiac cycle
$f_x$: Pressure sensor signal at the same point, x, within the cardiac cycle
$f_D$: Pressure sensor signal at diastole Equation 10 is solved to obtain a unique value for the ratio b/a. Now, the ratio of systolic to diastolic pressure is calculated using equation 11 as mentioned below.

$$\frac{P_S}{P_D} = \frac{1+\left(\frac{b}{a}\right)f_S}{1+\left(\frac{b}{a}\right)f_D} \quad (11)$$

Equations 9 and 11 are then solved to calculate $P_S$ and $P_D$.

Method-5 (Graphical Method):

This method is for the direct evaluation of subject specific arbitrary constants $P_0$ and $\beta$ of the empirical pressure-diameter equation, $P(t) = P_0 \exp(\beta D_{(t)}^2)$.

An arterial compliance probe with ultrasound transducer and force sensors (or one force sensor and any other blood pulse transducer) separated by a known distance are used to acquire signals for this method. Probe model in FIG. 6e is ideal for this method-5.

A linear relationship is assumed to convert the force sensor output waveform f(t) to pressure waveform P(t) as, $$P_{(t)} = a + b f_{(t)}$$

Now, $$a + b f_{(t)} = P_0 \exp(\beta D_{(t)}^2)$$

$$f_{(t)} = \kappa \cdot \exp(\beta D_{(t)}^2) + \lambda$$

Fit an exponential curve with $f_{(t)}$ as dependent variable and $D_{(t)}^2$ as independent variable. Obtain amplitude ($\kappa$), offset ($\lambda$, $\lambda \neq 0$) and damping ($\beta$) from the fitted exponential curve. Measure local pulse wave velocity using acquired pulse waves and hence pulse pressure, $\Delta P$.

$$\text{Calculate } P_0 \text{ using } P_0 = \frac{\Delta P}{e^{\beta D_S^2} - e^{\beta D_D^2}}$$

Now use $P_0$ and $\beta$ to calculate blood pressure using $$P(t) = P_0 \exp(\beta D_{(t)}^2)$$

Figure 8:
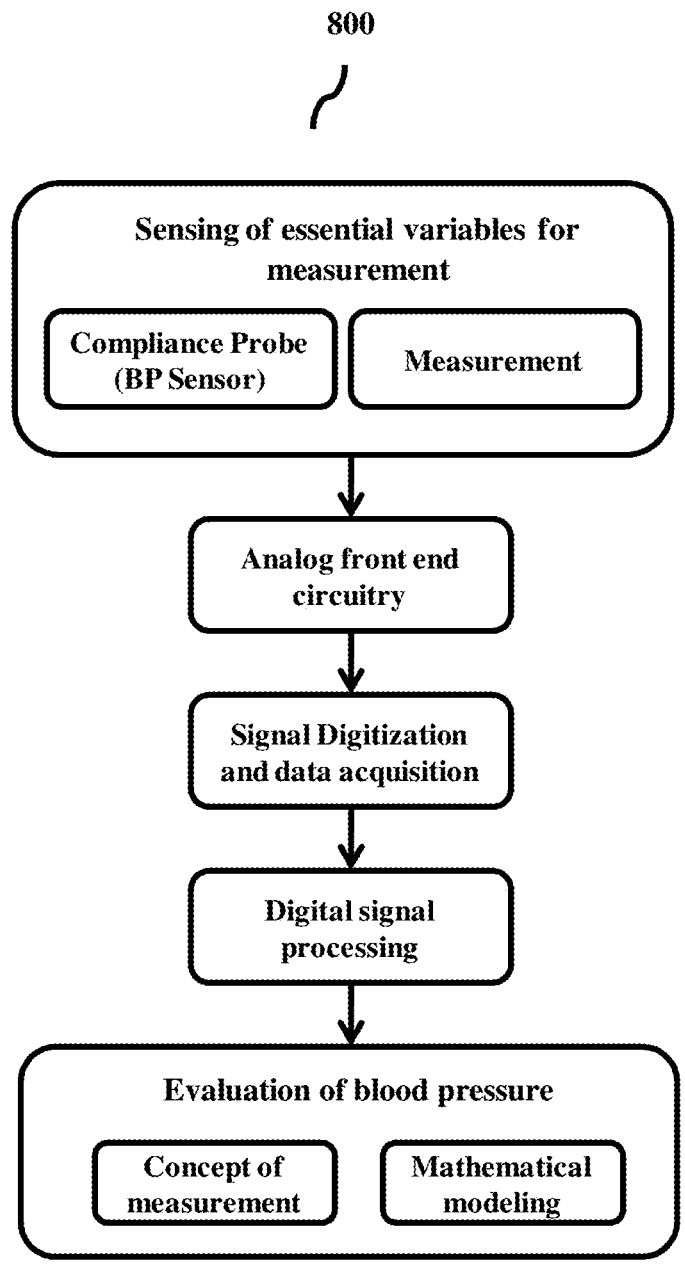
FIG. 8 is an overview of a system for cuff less measurement of BP of the subject, according to embodiments as disclosed herein.

FIG. 8 is an overview of the system 800 for cuff less measurement of blood pressure of the subject 108, according to embodiments as disclosed herein. In order to evaluate the Blood Pressure (BP) of the subject 108, the system 800 includes a compliance probe (BP sensor) which senses essential variables (local pulse wave velocity, end-diastolic diameter (Dd) and arterial distension ($\Delta D$) for measuring the blood pressure of the subject 108. In an embodiment, the compliance probe can be the pulse wave sensor and the ultrasound transducer. The sensed variables are fed into an analog front end circuitry which uses operational amplifiers, filter and so on. In an embodiment, the analog front end circuitry receives a pulse signal from the pulse wave sensor. The signal digitization performs a digitization operation to the pulse signal, such as an amplifying, filtering, and analog-digital converting operation, to generate a digital pulse signal. The digital pulse signal provides digitized values of local pulse wave velocity, end-diastolic diameter (Dd) and arterial distension ($\Delta D$). The data acquisition component obtains the values from the digitized pulse signal. Further, the digitized signals are processed using a digital signal processor. The processed digital signals are used to compute the blood pressure of the subject 108 based on measurement techniques and mathematical modeling. The measurement techniques include simultaneous measurement, sequential measurement.

Figure 9A:
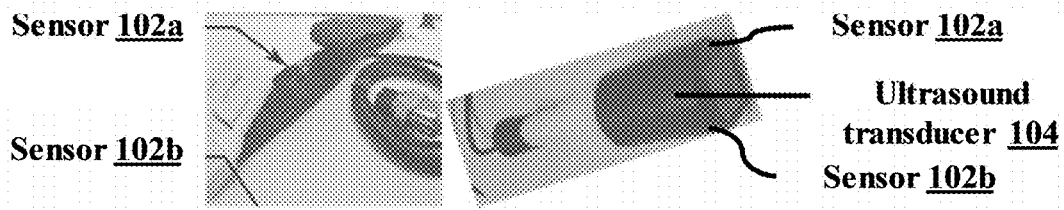
FIGS. 9a and 9b shows different probe designs for measuring the local PWV, the Dd, and the ΔD, according to embodiments as disclosed herein.
Figure 9B:
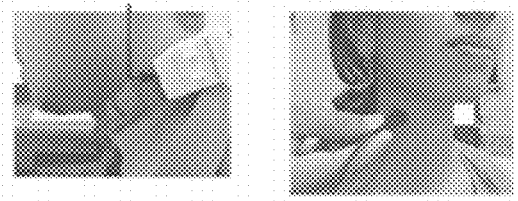

FIGS. 9a and 9b shows different probe designs for measuring the local PWV, the Dd, and the $\Delta D$, according to embodiments as disclosed herein. FIG. 9a shows the sensor 102a and the sensor 102b placed in a strap which can be worn in a neck of the subject 108. Further, the ultrasound transducer 104 is placed external to the strap and worn around the neck of the subject 108 to measure the local PWV, the Dd, and the $\Delta D$.

FIG. 9b shows a probe design including pulse wave sensors in the strap and the ultrasound transducer 104 which is external is positioned in the neck of the subject 108.

In an embodiment, the probe design used for measuring the local PWV, the Dd, and the $\Delta D$ can be a Bi-modal probe, a Tri-modal probe, a Bi-modal compliance probe. The details of the probe designs are given below.

Bi-Modal Probe:

The design includes the ultrasound transducer 104 for measurement of arterial dimensions, and dual pulse sensors to detect two pulse waveforms on either side of the ultrasound transducers 104. Identical pulse sensors can be used to ensure match between the two waveforms detected for local PWV measurement. Several variations of the bi-modal probe and Tri-modal probe are given below.

Ultrasound—Pressure Sensors:

This probe utilizes surface pressure sensors to detect dual pressure pulse waveforms from a superficial artery. A single element ultrasound transducer 104 will be located in the probe to measure arterial dimensions.

Ultrasound—Magnetic Plethysmograph Sensors:

This probe utilizes dual Magnetic Plethysmograph (MPG) sensors to capture the two pulse waveforms. The MPG typically consists of a small magnet (electromagnet/permanent one) that establishes an ambient field and a magnetic field sensor (such as a Hall sensor or a Giant Magneto Resistance sensor) to detect the pulse waveform. A single element ultrasound transducer will be located in probe to measure arterial dimensions.

Ultrasound—Photo Plethysmograph Sensors:

This probe utilizes dual photo plethysmograph (PPG) sensors to capture the two pulse waveforms. The PPG sensors utilize a light emitting diode and a photo detector to capture a pulse waveform. Reflectance based PPG sensor designs will be adopted. The single element ultrasound transducer 104 will be located in probe to measure arterial dimensions.

Tri-Modal Probe:

This probe utilizes one pressure sensor and one Magnetic Plethysmograph sensor (MPG) to capture two pulse waveforms required for local PWV measurement. This allows quick and reliable capture of both waveforms, with minimal cross sensitivity between the two sensors. Although, the pressure sensor can capture a reliable waveform from the superficial artery site, the MPG can capture a waveform from a site where the artery is slightly deeper. This improves practical reliability of the probe. The single element ultrasound transducer will be located in probe to measure arterial dimensions.

Bi-Modal Compliance Probe:

This probe has the ECG electrode integrated around the single element ultrasound transducer 104. This may be used for measuring arterial dimensions, and also local PWV by performing two successive measurements at two sites along any superficial artery.

In an embodiment, the proposed method uses a smart probe to measure and compute the blood pressure of the subject 108. The probe computes blood pressure based on mathematical models.

Figure 9C:
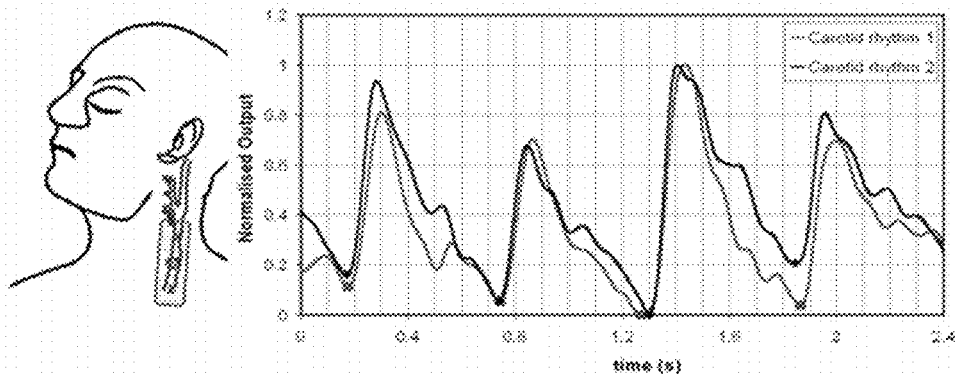
FIG. 9c shows the local PWV waveform generated using a dual element probes, according to embodiments as disclosed herein.

FIG. 9c shows the local PWV waveform generated using dual element probes, according to embodiments as disclosed herein. The proposed method simultaneously measures dual pulse waveforms without using external ECG connections. In an embodiment, the dual pulse waveforms are measured using either the Tri-modal or Bi-modal probe.

Figure 9D:
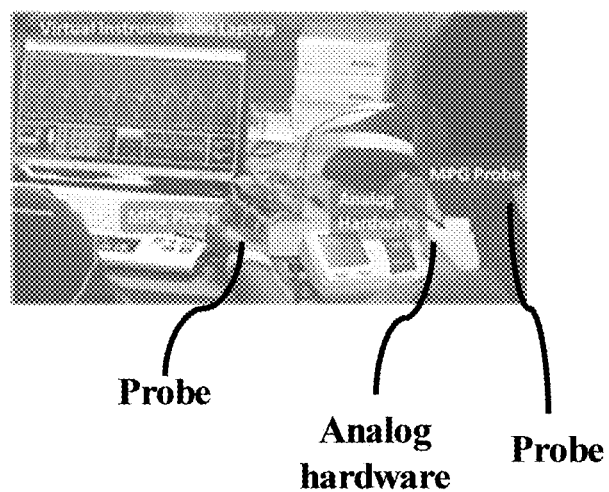
FIGS. 9d and 9e shows instrumentation for cuff less BP measurement of the subject utilizing probes, and hardware components, according to embodiments as disclosed herein.
Figure 9E:
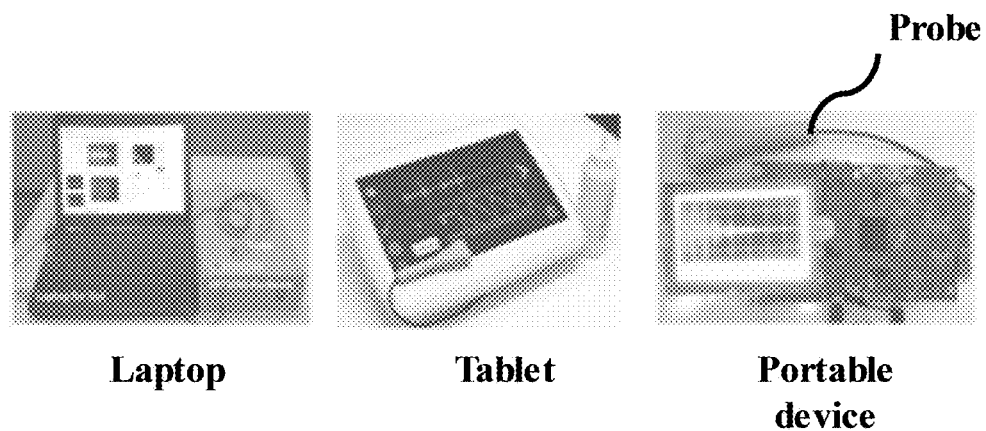

FIGS. 9d and 9e shows instrumentation for evaluating blood pressure of the subject 108 utilizing probes, and hardware components, according to embodiments as disclosed herein. FIG. 9d shows a desktop hardware and instrument for measuring the local PWV, the Dd and the ΔD. In an embodiment, the pulse wave sensors are placed within the strap positioned around the neck of the subject 108. The FIG. 9d depicts using two probes to measure PTT across larger distances. In an embodiment, the pulse wave sensors are the MPG sensors. Further, the analog hardware obtains the signals from the sensor and processes the signals. The desktop hardware connected to the sensors shows the dual pulse waveforms.

FIG. 9e shows the instrumentation for computing the blood pressure of the subject 108 after receiving the local PWV, the Dd and the ΔD from the probes connected to a tablet, laptop or any other portable devices.

The embodiments disclosed herein can be implemented through at least one software program running on at least one hardware device and performing network management functions to control the elements. The elements shown in FIGS. 1, 2a, 2b, 4, 5, 6a-6c, 7, 8 and 9a-9e include blocks which can be at least one of a hardware device, or a combination of hardware device and software module.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A system for cuff-less calibration free measurement of blood pressure (BP) of a subject, the system comprising:
   a probe comprising:
      a first sensor;
      a second sensor spaced at a distance from said first sensor; and
      a third sensor;
      an ultrasound transducer connected with said first sensor and said second sensor, wherein the ultrasound transducer is placed at a center of the third sensor in said probe and in between said first sensor and said second sensor; and
      a controller unit connected to said probe;
   wherein said first sensor and second sensor are configured to measure a local pulse wave velocity (PWV) of an arterial wall of said subject;
   wherein said ultrasound transducer configured to measure a change in a change in an arterial dimensions over a cardiac cycle of said arterial wall of said subject, wherein said arterial dimensions include an arterial distension and an end-diastolic diameter; and
   wherein said third sensor is configured to provide a feedback to said controller unit to measure BP of said subject and wherein said controller unit is configured to measure the blood pressure (BP) waveform at the artery measurement site of said subject based on said local PWV and said change in arterial dimensions in each heart beat.

2. The system of claim 1, wherein said ultrasound transducer is coupled to said first sensor, wherein said system is configured to simultaneously acquire a surface pressure waveform and an arterial distension waveform from same location.

3. The system of claim 2, wherein an output from said first sensor and said second sensor or said surface pressure waveform and said arterial distension waveform are used to measure said local PWV.

4. The system of claim 1, wherein said first sensor and said second sensor are configured to measure said local PWV of said arterial wall of said subject by:

detecting a first pulse waveform at first site along said artery wall;

detecting a second pulse waveform at a second site along said artery wall, wherein said first site and said second site is spaced at a distance; and measuring said local PWV by computing a time difference between said first pulse waveform and said second pulse waveform.

5. The system of claim 1, wherein said ultrasound transducer is configured to measure said arterial dimensions over said cardiac cycle and the said arterial diameter waveform of said arterial wall of said subject by:

sending ultrasound signals through body of said subject;

obtaining reflected ultrasound signals from a near arterial wall and a far arterial wall;

converting said ultrasound signals to corresponding voltage pulses;

splitting said voltage pulses into said plurality of frames;

detecting a location of said arterial wall based on a motion profile signal identified from said plurality of frames in said plurality of voltage pulses;

tracking motion of said arterial wall from a frame to a subsequent frame, wherein said frame and said subsequent frame is from said plurality of frames;

measuring said arterial distension based on a difference between a near arterial wall and a far arterial wall motion; and measuring said end-diastolic diameter across a vessel towards end of a diastole.

6. A hand-held device for a cuff-less calibration free Blood Pressure (BP) measurement of a subject, comprising:

a probe configured to be held proximal to skin of said subject, wherein said probe comprises:

a first sensor;

a second sensor spaced at a distance from said first sensor;

a third sensor;

an ultrasound transducer connected with said first sensor and said second sensor, wherein the ultrasound transducer is placed at a center of a third sensor in said probe; and an ultrasound transducer connected with said first sensor and said second sensor, wherein the ultrasound transducer is placed at a center of the third sensor in said probe and in between said first sensor and said second sensor; and a controller unit connected to said probe;

wherein said first sensor and second sensor are configured to measure a local pulse wave velocity (PWV) of an arterial wall of said subject;

wherein said ultrasound transducer configured to measure a change in a change in an arterial dimensions over a cardiac cycle of said arterial wall of said subject, wherein said arterial dimensions include an arterial distension and an end-diastolic diameter;

wherein said third sensor is configured to provide a feedback to said controller unit to measure BP of said subject and wherein said controller unit is configured to measure the blood pressure (BP) waveform at the artery measurement site of said subject based on said local PWV and said change in arterial dimensions in each heart beat.

7. The hand-held device of claim 6, wherein said ultrasound transducer is placed in between said first sensor and said second sensor.

8. The hand-held device of claim 6, wherein said ultrasound transducer is coupled to said first sensor, wherein said hand-held device is configured to simultaneously acquire a surface pressure waveform and an arterial distention waveform from same location.

9. The hand-held device of claim 8, wherein an output from said first sensor and said second sensor or said surface pressure waveform and said arterial distention waveform are used to measure said local PWV.

10. The hand-held device of claim 6, wherein said first sensor and said second sensor are configured to measure said local PWV of said arterial wall of said subject by:

detecting a first pulse waveform at first site along said artery wall;

detecting a second pulse waveform at a second site along said artery wall, wherein said first site and said second site is spaced at a distance; and measuring said local PWV by computing a time difference between said first pulse waveform and said second pulse waveform.

11. The hand-held device of claim 6, wherein said ultrasound transducer is configured to measure said change in arterial dimensions over said cardiac cycle of said arterial wall of said subject by:

sending ultrasound signals through body of said subject;

obtaining reflected ultrasound signals from a near arterial wall and a far arterial wall;

converting said ultrasound signals to corresponding voltage pulses;

splitting said voltage pulses into said plurality of frames;

detecting a location of said arterial wall based on a motion profile signal identified from said plurality of frames in said plurality of voltage pulses;

tracking motion of said arterial wall from a frame to a subsequent frame, wherein said frame and said subsequent frame is from said plurality of frames;

measuring said arterial distension based on a difference between a near arterial wall and a far arterial wall motion; and measuring said end-diastolic diameter across a vessel towards end of a diastole.

* * * * *